(12) United States Patent
Sheikh

(10) Patent No.: US 9,572,516 B1
(45) Date of Patent: Feb. 21, 2017

(54) APPLICATION AND METHOD FOR PRODUCING IMAGES OF MOVING JOINTS

(71) Applicant: Babak Sheikh, Weston, FL (US)

(72) Inventor: Babak Sheikh, Weston, FL (US)

( * ) Notice: Subject to any disclaimer, the term of this patent is extended or adjusted under 35 U.S.C. 154(b) by 656 days.

(21) Appl. No.: 13/960,799

(22) Filed: Aug. 6, 2013

(51) Int. Cl.
*A61B 5/00* (2006.01)
*A61B 5/055* (2006.01)

(52) U.S. Cl.
CPC .................................. *A61B 5/0555* (2013.01)

(58) Field of Classification Search
CPC .................................................... A61B 5/055
See application file for complete search history.

(56) References Cited

U.S. PATENT DOCUMENTS 6,345,193 B2 * 2/2002 Dutto ............................... 5/601
2012/0093384 A1 * 4/2012 Goto ................ G01R 33/56509
382/131

* cited by examiner

*Primary Examiner* — Mark Remaly
(74) *Attorney, Agent, or Firm* — Ronald V. Davidge

(57) ABSTRACT

A joint of a patient is scanned using MRI apparatus, and images of the joint area are produced as a body part of the patient is moved into a particular position known to cause a problem in the joint. The patient may walk or run on a treadmill during the process, or the body part may be supported on a surface causing or allowing such movement.

4 Claims, 14 Drawing Sheets

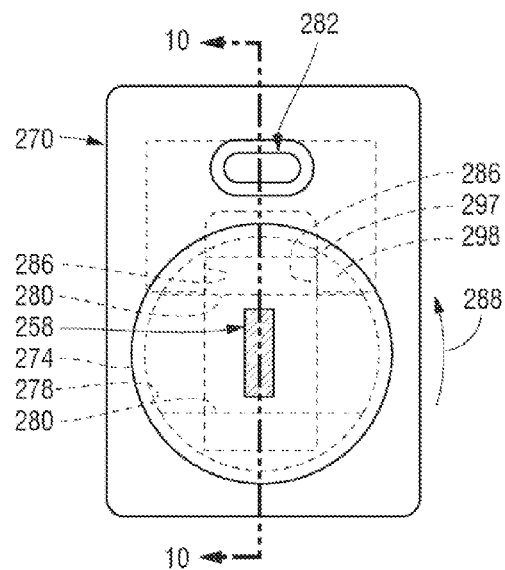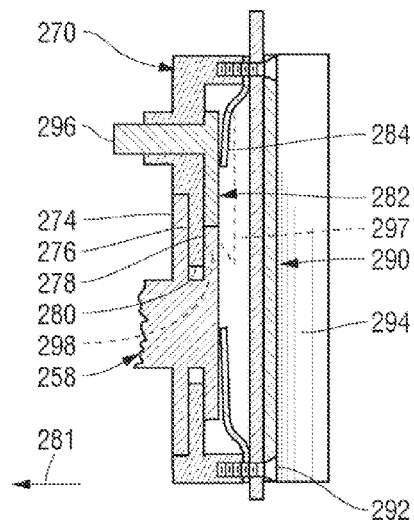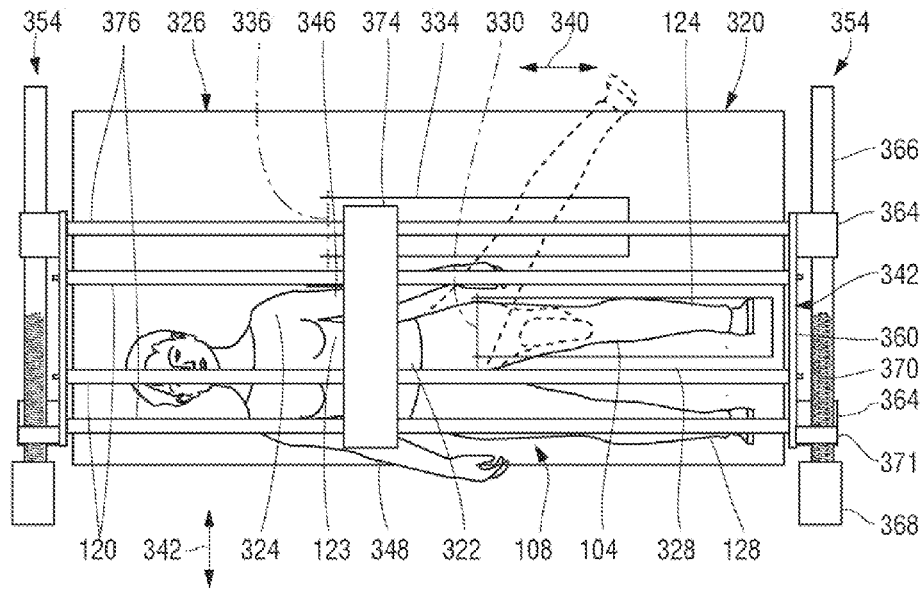

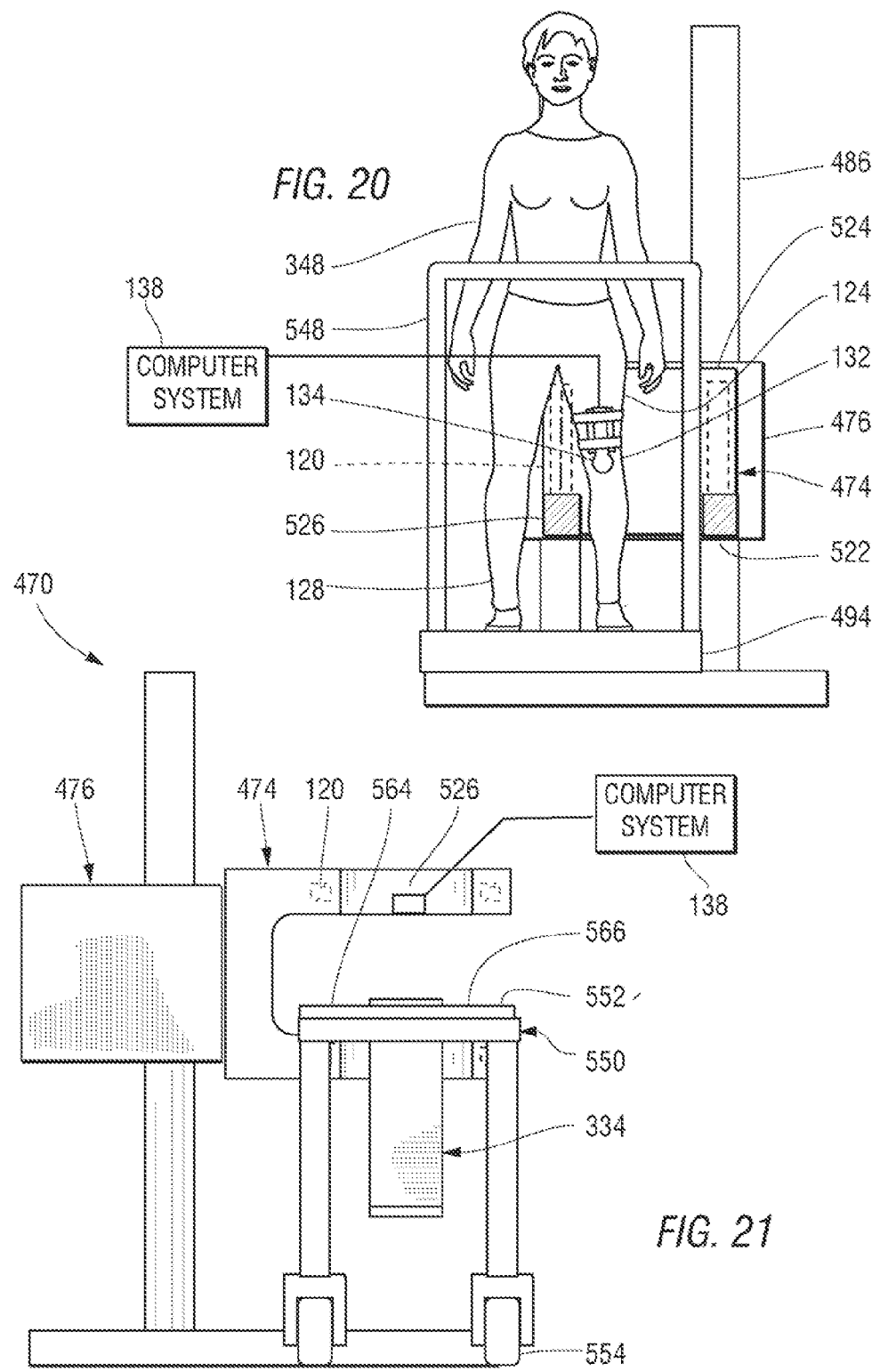

APPLICATION AND METHOD FOR PRODUCING IMAGES OF MOVING JOINTS

RELATED APPLICATIONS

Not applicable.

FEDERALLY SPONSORED RESEARCH OR DEVELOPMENT

Not applicable.

BACKGROUND OF THE INVENTION

1. Field of the Invention

This invention relates to forming images of joint structures, and, more particularly, to forming such images as body members connected to the joint structures are moved.

2. Summary of the Background Information

Magnetic resonance imaging (MRI), which is additionally called nuclear magnetic resonance imaging (NMRI), or magnetic resonance tomography (MRT), is a medical imaging technique used to visualize internal structures of the body, making use of the property of nuclear magnetic resonance (NMR) to image nuclei of atoms inside the body in a process known to create more detailed images of the human body than possible with X-rays. A conventional MRI scanner includes a large, powerful magnet, extending around a cavity in which the patient 108 lies, while a magnetic field formed by the magnet aligns the magnetization of certain atomic nuclei within the body, and while radio frequency magnetic fields are applied to systematically alter the alignment of this magnetization. This causes the nuclei within certain atoms in the body to produce a rotating magnetic field detectable by the scanner, which in turn causes information to be recorded for constructing an image of the scanned area of the body. Magnetic field gradients cause nuclei at different locations to process at different speeds, allowing spatial information to be recovered using Fourier analysis of the measured signal. By using gradients in different directions, two-dimensional images or three-dimensional volumes can be obtained in any arbitrary orientation. The resulting images display good contrast between the different soft tissues of the body, making the MRI process especially useful in imaging the brain, muscles, heart, and cancers compared with other medical imaging techniques such as computed tomography (CT) or X-rays. Furthermore, an important advantage for MRI arises from the fact that unlike CT scans or traditional X-rays, MRI does not expose the patient to ionizing radiation.

For some time it has been possible to make moving images of the heart and other organs from MRI scans, with such images being displayed, for example, on the Internet. However, in the past, such images were reconstructed after completion of the scanning process by combining images derived from a number of repetitive actions (such as a heart beat occurring while the subject holds his breath) into a motion picture sequence.

More recently, a process, known as "Real-time MRI," has been developed for making pictures of moving objects using MRI in real time, so that the images are displayed during the scanning. Because the generation of image data was based on a time-consuming process of data reconstruction from scanned data, in what is known as 'k-space," real-time MRI was formerly possible only with low image quality or low temporal resolution. In the past such images could only be formed at a rate of about one per second.

This limitation has now been eliminated, particularly through the use of an iterative reconstruction algorithm that alleviates problems caused by undersampling, and with radial FLASH MRI, in an improved process offering rapid and continuous data acquisition, motion robustness, and tolerance to undersampling. In particular, improved techniques integrates the data from multiple receive coils, in a process also known as parallel MRI, and exploits the redundancy in a sequence of images, reducing the effects of data undersampling by an order of magnitude, so that high-quality images may be obtained from of as little as 5 to 10% of the data required for a normal image reconstruction. For example, a temporal resolution of 20 to 30 milliseconds can now be achieved achieved, along with an in-plane resolution of 1.5 to 2.0 mm.

While, in principle this technique can be implemented with most current scanners, a practical limitation lies in the amount of computing power required to perform the real-time reconstruction of the images. Improvements in the algorithms used for image reconstruction and the use of parallel computer processors are significantly reducing time required to produce one minute of images displaying motion from one half hour.

The patent literature includes a number of examples of imaging apparatus and image data processing methods for increasing the speed at which images can be reconstructed and for increasing the resulting resolution of the images. For example, a magnetic resonance (MR) imaging apparatus and technique is described as exploiting spatial information inherent in a surface coil array to increase MR image acquisition speed, resolution and/or field of view. Partial signals arc acquired simultaneously in the component coils of the array and formed into two or more signals corresponding to orthogonal spatial representations. In a Fourier embodiment, lines of the k-space matrix required for image production are formed using a set of separate, preferably linear combinations of the component coil signals to substitute for spatial modulations normally produced by phase encoding gradients. The signal combining may proceed in a parallel or flow-through fashion, or as post-processing, which in either case reduces the need for time-consuming gradient switching and expensive fast magnet arrangements. In the post-processing approach, stored signals are combined after the fact to yield the full data matrix. In the flow-through approach, a plug-in unit consisting of a coil array with an on board processor outputs two or more sets of combined spatial signals for each spin conditioning cycle, each directly corresponding to a distinct line in k-space. This partially parallel imaging strategy, dubbed Simultaneous Acquisition of Spatial Harmonics (SMASH), is readily integrated with many existing fast imaging sequences, yielding multiplicative time savings without a significant sacrifice in spatial resolution or signal-to-noise ratio. An experimental system achieved two-fold improvement in image acquisition time with a prototype three-coil array, and larger factors are achievable with then coil arrangements.

In another example from the patent literature, a method of and system are described in which the method comprises acquiring a plurality of magnetic resonance signals from a receiver coil array placed about a subject in the MRI system, where the receiver coil array has a plurality of receiver elements arranged in rows and, during application of a readout gradient in a frequency encoding direction, shifting receiver frequencies by a selectable amount for each row of the array in order to shift a limited field of view in the frequency encoding direction.

In yet another example from the patent literature, an MRI system produces a three-dimensional. Image by acquiring NMR signals that fully sample a central region as a set of asymmetric radial sectors. The NMR signals are acquired with a plurality of receive channels and coils. An image is reconstructed using a homodyne reconstruction combined with SENSE nrocessine.

The patent literature further describes the use of a Halbach magnet array in place of the conventional, very large, horseshow magnet within MRI apparatus. In general, a Halbach magnet array is an arrangement of magnets that augments the magnetic field on one side of the arrangement while canceling the magnetic field, to nearly a zero level, on the other side.

FIG. 1 is a perspective view of MRI apparatus to described in prior art patent documents. The apparatus 10 includes a Halbach array 12 of magnetic structures 14 located at corners of a square, in which probe apparatus 17 is held to receive signals for processing. Each of the magnetic structures 14 includes a dipole magnet, generating a magnetic field extending transverse to its direction of elongation, indicated by arrow 16. Each of the magnetic structures 14 may include one or more permanent magnets, and may additionally or alternatively include one or more electromagnetic coils, which may be held within a tube filled, for example, with liquid helium to achieve superconductivity.

FIG. 2 is a schematic cross-sectional transverse view of the apparatus 10, taken in as indicated by section lines 2-2 in FIG. 1, with an arrow 18 showing a direction of the magnetic field extending transversely within each of the magnetic structures 14. Transverse magnetic fields 20 extend outward from each of the magnetic structures 14, with fields formed in the direction of arrow 22 a central region 24 surrounded by the magnetic structures 14 being strengthened, and with magnetic fields in a region 26 outside the Halbach array 12 being substantially reduced, as reflected in the increased distance between flux lines in the figure.

FIG. 3 is a schematic cross-sectional transverse view of the apparatus 10 showing the magnetic structures 14 oriented so the transverse magnetic fields within the magnetic structures 14 are oriented as shown by arrows 30 to produce a magnetic field in the direction of arrow 32 within the central region 24.

FIG. 4 is an elevation of a hand-held MRI probe 40, described in the patent literature, which includes a coil section 42 having an imaging coil It is noted that the lack of exposure to ionizing radiation during the MRI process makes it possible for an individual to remain with the patient during the process, and that the probe 40 can be held close to the tissues being scanned, with a resulting improvement in the quality of the images being produced.

d to allow a patient, as you described, show what was happening when he had a transient pain or discomfort. The main problem in making such pictures appears to be computer processing time to get the images ready for viewing, since it takes about a half hour to process about a minute of real time film, and limitations on the resolution of the images, which can be expected to limit the resolution of the images. The need for an open structure does not

SUMMARY OF THE INVENTION

According to one aspect of the invention, a method is provided for examining a joint region. The method includes: determining that a problem develops within the joint region when a first body part adjacent the joint region is formed into a particular position; placing thee joint region in a central region within magnetic resonance imaging (MRI) apparatus, including a magnetic structure disposed at each side of the central region, and an additional placed adjacent the central region, with the body part disposed within the additional space; moving the body part adjacent the joint region into the particular position while causing a nuclear magnetic resonance (NMR) signal to be formed within the central region; receiving the NMR signal within a probe assembly within the central region and transmitting a signal including data describing structures within the joint region from the probe assembly; and generating and displaying a viewable image of the joint region from the signal transmitted from the probe assembly.

If the joint region moves substantially within the central region as the body part is moved into the particular position, the probe is attached to the patient's body adjacent the joint region to move with the joint region. The body part may be moved into the particular position as the patient walks or runs on a treadmill disposed within the additional area. While walking or running on the treadmill, the patient may straddle a central structure shielding a portion of the magnetic structures. Alternately, the method may additionally include placing the patient on a table extending within the MRI apparatus adjacent the central region and lowering a door within the table to allow the body part to be moved into the preferred position.

In accordance with a second aspect of the invention, apparatus is provided, including a a magnetic resonance imaging (MRI) device, a probe assembly, and a computer system. The MRI device has an overall magnetic structure with portions on each side of a central region, and electrical circuits, producing NMR (nuclear magnetic resonance) signals within the central region. The probe assembly, which is configured for attachment to a portion of a human body, includes a probe held close to a joint within the human body as the joint is moved within the central region. The probe is configured to receive NMR signals and to transmit an output signal including information derived from the NMR signals. The computer system indicates features of material held within a joint moving within the central region from the output signal from the probe.

For example, the apparatus may additionally include a treadmill disposed below the central region, with the treadmill being configured to move a joint within the leg of a person walking or running on the treadmill within the central region. Then, the probe is configured for attachment to the leg, with the probe being held close to a joint, such as the knee or ankle, within the leg. For example, the probe assembly may include a cradle configured to be strapped to the leg of a patient with the probe being held near the knee of the patient. The treadmill may include a web, arranged to be moved in a first direction by the patient, having a center extending in the first direction, while the overall magnetic structure includes a Halbach magnet array having four elongated magnetic structure arranged at corners of a square extending around the central region, with two of the elongated magnetic structures being disposed above the center of the web, and with the elongated magnetic structures being arranged so that a knee of a patient walking on the treadmill moves within the central region. Alternately, the treadmill may include a pair of webs, arranged to be moved together by the patient, having a space between the webs, with the central region being formed adjacently above one of the webs. The magnetic structure may be movable vertically between a position in which the central region is arranged to extend through a knee of a patient walking on the treadmill and a position arranged to cause the central region to extend through an ankle of a person walking on the treadmill.

In accordance with a third aspect of the invention, apparatus is provided, including a a magnetic resonance imaging (MRI) device, a probe assembly, a platform, a supporting surface, and a computer system. The MRI device has an overall magnetic structure with portions on each side of a central region, and electrical circuits, producing NMR (nuclear magnetic resonance) signals within the central region. The probe assembly is configured to receive NMR signals and to transmit an output signal including information derived from the NMR signals. The platform is configured to hold a body of a patient so that a joint of the patient, such as the shoulder or knee, is held within the central region. The supporting surface is configured to support a body part extending from the joint as the body part is moved with the joint held within the central region. The computer system indicates features of material held within a joint moving within the central region from the output signal from the probe.

For example, the platform may be configured to support a body of a person lying on a first side, while the supporting surface includes a surface extending laterally away from the person, being spaced above the platform at a distance chosen to support movement of an arm opposite the first side along the supporting surface. Alternately, the platform may include a flat table surface, while the supporting surface includes an arm-dropping door pivotally mounted to move downward from the platform, and configured to support an arm while a should is held in the central region. A leg-dropping door may additionally be included.

In accordance with a fourth aspect of the invention, apparatus is provided, including a carriage mounted to pivot about a pivot axis, an MRI device, a probe assembly, and a computer system. The MRI device includes an overall magnetic structure held within the carriage and further includes electrical drive means causing magnetic fields within the central region to produce NMR signals. The overall magnetic structure includes a Halbach magnet array having four elongated magnetic structures, arranged at corners of a square to extend in a common direction around a central region, with the common direction being perpendicular to the pivot axis. A first slot extends through the carriage parallel to the common direction, while a second slot extends through the carriage perpendicular to the common direction, and while a third slot extends inwardly into the carriage in perpendicular to the first and second slots.

The carriage may additionally include an open end, with open spaces between all four elongated magnetic structures, and a closed end, with support structures extending between two adjacent pairs of elongated magnetic structures, and a closed end. The apparatus may additionally include a treadmill, with the carriage being mounted to be vertically movable above the treadmill. Alternately, the apparatus may additionally include a platform configured to hold a body of a patient so that a joint of the patient is held within the central region; and a a supporting surface configured to support a body part extending from the joint as the body part is moved with the joint held within the central region.

BRIEF DESCRIPTION OF THE DRAWINGS

These and other aspects of the invention will be made apparent by reading the following specification in conjunction with the accompanying figures, in which:

FIG. 9 is an elevation of a connection member within the probe apparatus of FIG. 8, shown releasably holding a portable probe therein;

FIG. 10 is a cross-sectional elevation of the connection member of the connection member of FIG. 9, taken as indicated by section lines 10-10 therein;

FIG. 11 is a plan view of MRI apparatus made and used for scanning a hip or shoulder in accordance with a second embodiment of the invention;

FIG. 20 is a partly sectional end elevation of the MRI apparatus of FIG. 17, shown as used with a treadmill for scanning a knee;

FIG. 21 is an end elevation of the MRI apparatus of FIG. 17, shown as used with a table built in accordance with the invention;

DETAILED DESCRIPTION OF THE INVENTION

Figure 5:
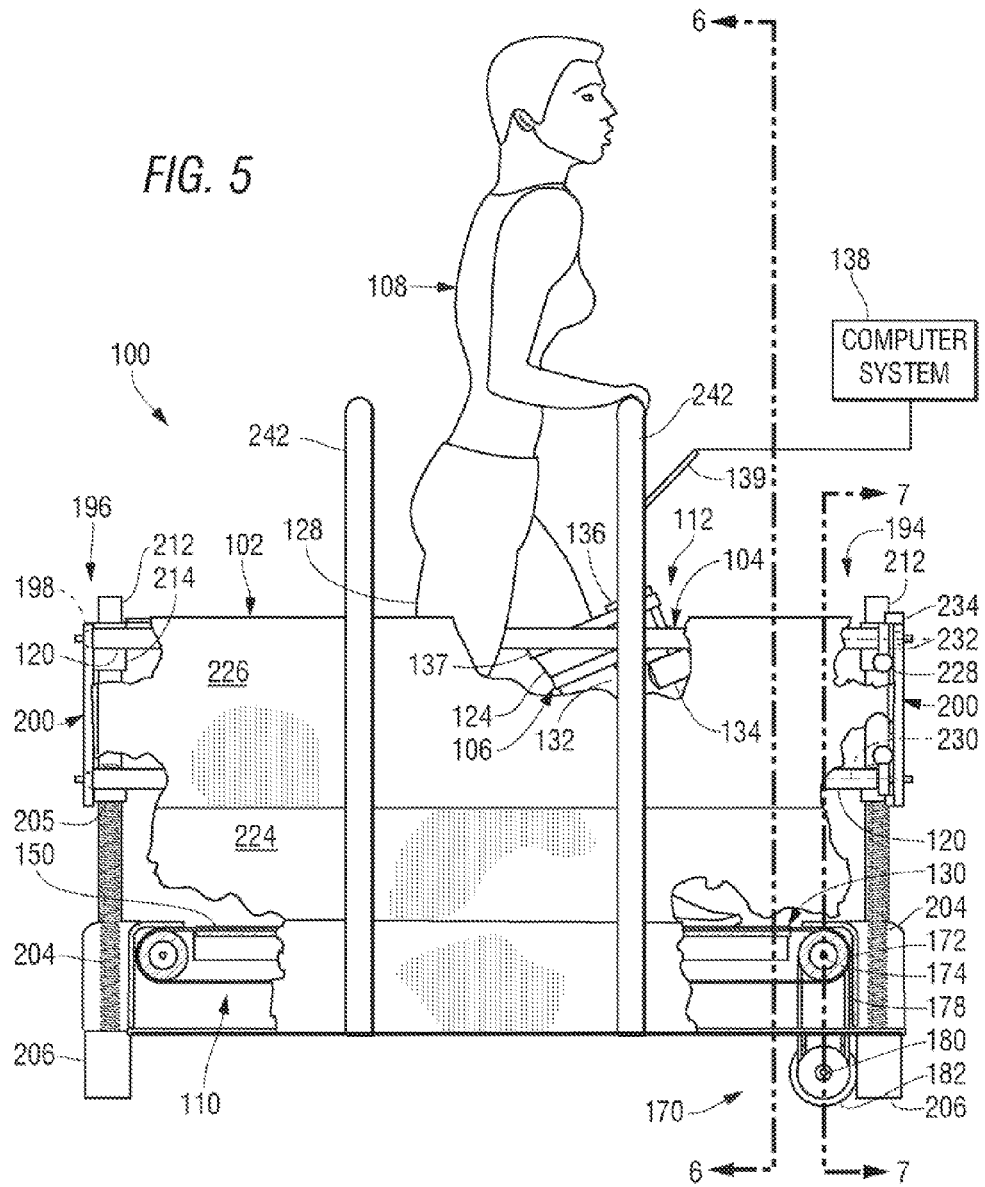
FIG. 5 is a longitudinal elevation of MRI apparatus built and used in accordance with a first embodiment of the present invention.
Figure 6:
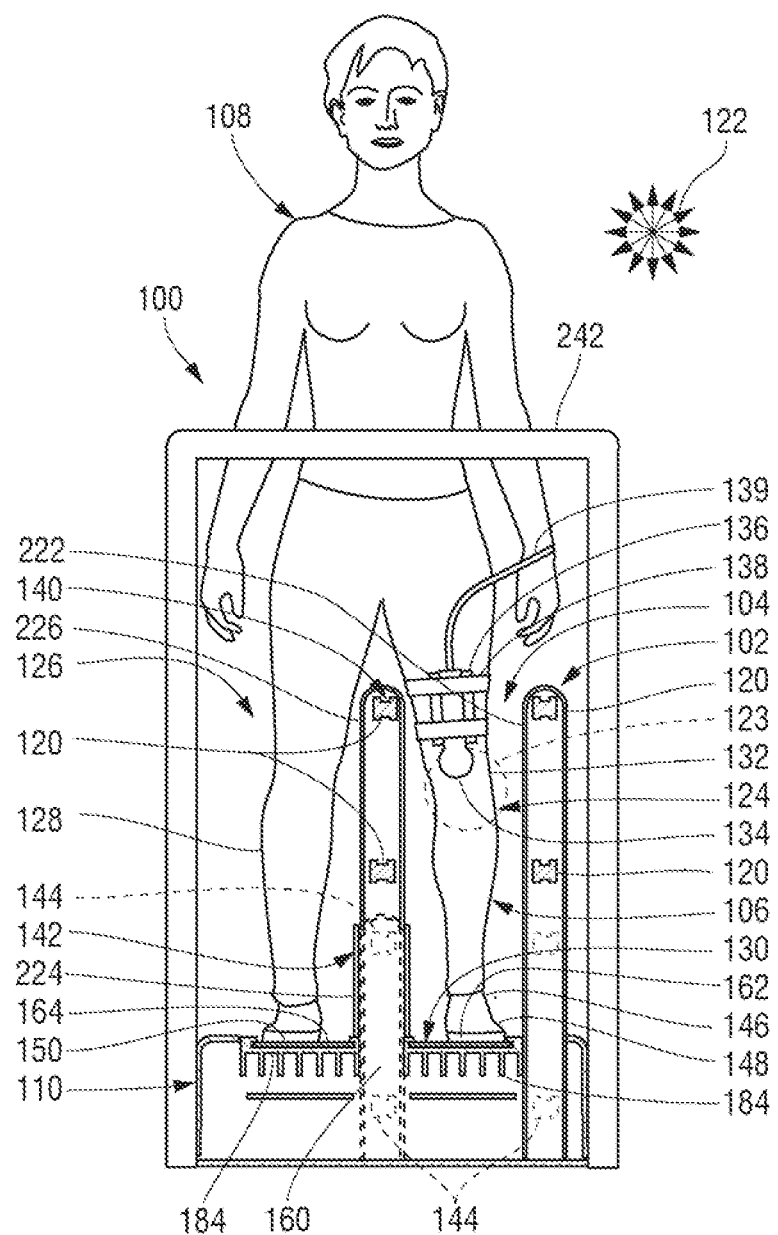
FIG. 6 is a transverse cross-sectional elevation of the MRI apparatus of FIG. 5, taken as indicated by section lines 6-6 therein.

FIGS. 5 and 6 are views of is a longitudinal cross-sectional elevation of MRI apparatus 100 built and used in accordance with a first embodiment of the present invention, with FIG. 5 being a longitudinal elevation of the MRI apparatus 100, while FIG. 6 is a transverse cross-sectional view thereof, taken as indicated by section lines 6-6 in FIG. 5. The MRI apparatus 100 includes an overall magnetic structure 102 disposed at opposite sides of an imaging slot 104, in which a portion 106 of a body of a patient 108 is placed for scanning, exercise apparatus 110, by means of which the body portion 106 is moved, and a probe 112.

Figure 1:
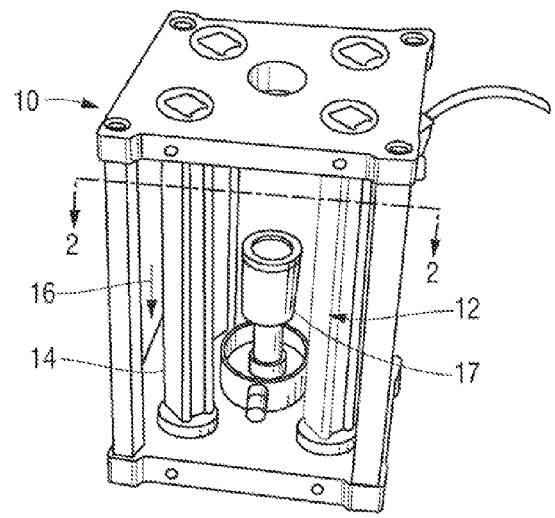
FIG. 1 is a perspective view of a Halbach magnet array described as MRI apparatus in the patent literature.
Figure 2:
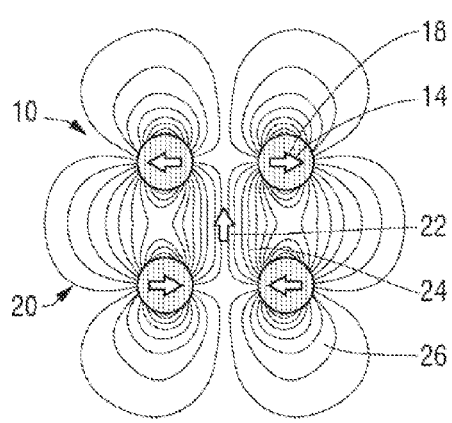
FIG. 2 is a first schematic cross-sectional transverse view of the magnet array of FIG. 1, taken as indicated by section lines 2-2 therein.
Figure 3:
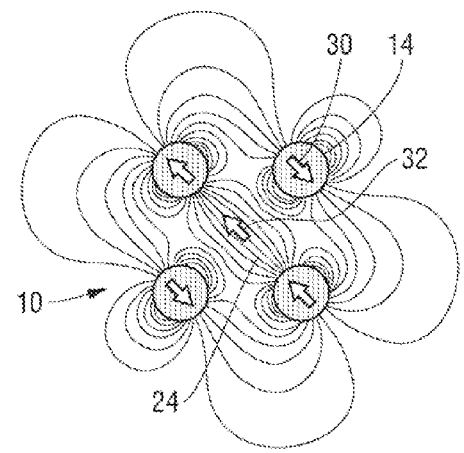
FIG. 3 is a second schematic cross-sectional transverse view of the magnet array of FIG. 1, showing magnetic structures therein in a different orientation.
Figure 4:
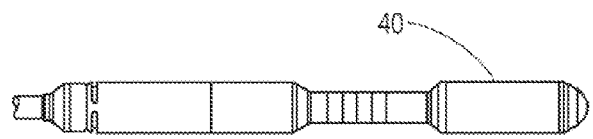
FIG. 4 is an elevation of a hand-held MRI probe described in the patent literature.

In the example of the MRI apparatus 100, the overall magnetic structure 102 includes four elongated magnetic structures 120 that together form a Halbach array, with centers of the elongated magnetic structures 120 being transversely disposed at corners of a square, with magnetic flux lines extending outward from each of the elongated magnetic structures 120 in the transverse directions of arrows 122, to be concentrated within a central region 123 as generally described above in reference to FIGS. 1-3. Each of the elongated magnetic structures 120 may include permanent magnets and/or electromagnetic coils, which may be cryogenically cooled using, for example, liquid helium to achieve superconductivity. The magnetic materials within each of the elongated magnetic structures 120 together form a dipole magnet, with poles extending along opposite sides of the elongated magnetic structure 120. The elongated magnetic structures 120 are disposed on opposite sides of the imaging slot 104, in which a portion 106 of the body of the patient 108, such as a leg 124, is placed for imaging. The MRI apparatus 100 additionally includes a passive space 126, which is not itself used for imaging, but which provides for placement of another body part, such as the other (right) leg 128, allowing natural movements, such as waling and running, to be performed during the scanning process. Additionally, in the example of the MRI apparatus 100, the exercise apparatus 110 comprises a treadmill 130, forming a lower surface of the imaging slot 104, so that the patient 108 can walk or run as images of from the leg 124 are formed by the MRI apparatus 100.

In the example of FIGS. 5 and 6, the MRI apparatus 100 is configured to provide images of a knee 132 within the patient's leg 124 during walking or running, using signals generated within a portable probe 134 fastened to the leg 124 to be disposed adjacent the knee 132. In general, the MRI process relies on the detection of faint nuclear magnetic resonance (NMR) signals from protons in the presence of a strong magnetic field after excitation by a radio frequency signal. The NMR signals are detected using antennae generally called "coils". Since the NMR signals are extremely faint, the ability for a coil to detect these signals tends to increase with decreasing distance between the coil and the tissue being imaged. Furthermore, coils located closer to the tissue being imaged are known to have a higher signal-to-noise ratio (SNR) than coils positioned further away from the tissue, even if the coils that are positioned close to the tissue of interest are smaller than those positioned further away. In the MRI apparatus 100, fastening the portable probe 134 to a portion 106 of the body of the patient 108 near the area, such as the knee 132, to be scanned allows placement of the portable probe 134 in close proximity to the area to be scanned and furthermore allows the special relationship between the portable probe 134 and at least a portion of the area being scanned to be held despite movement of the patient's body within the imaging slot 104. For example, the portable probe 134 is attached to a support structure 136 fastened to the leg 124 by a pair of straps 137. The portable probe 136 is electrically connected to circuits within the MRI apparatus 100, including a computer system 138 using signals from the portable probe 146 to generate and display data representing structures of the knee 132, by a signal cable 139.

The elongated magnetic structures 120 are preferably movable between an upper position 140, in which they are shown, and in which they are used to provide a magnetic field for scanning the knee 132, and a lower position 142, in which they are indicated by dashed lines 144, and in which they are used to provide a magnetic field for scanning the ankle 146 and foot 148, with the lowermost elongated magnetic structures 120 being moved below the upper surface 150 of the treadmill 130, placing the central region 123 of the elongated magnetic structures 120 in a position including the ankle 146 and the foot 148, as the foot 148 is moved in contact with the treadmill 130, in a concentrated magnetic field. So that the elongated magnetic structures 120 can be moved into the lower position 142, the treadmill 130 is longitudinally divided about central space 160, providing a first movable web 162 extending under the imaging slot 104 and a second movable web 164 extending under the passive space 126.

Figure 7:
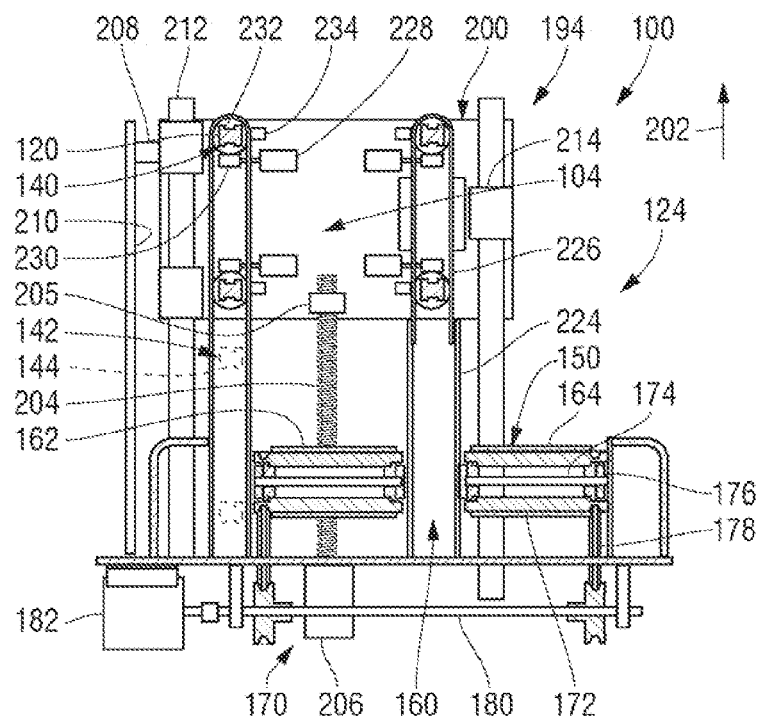
FIG. 7 is a fragmentary transverse cross-sectional elevation of the MRI apparatus of FIG. 5, taken as indicated by section lines 7-7 therein.

FIG. 7 is a fragmentary transverse cross-sectional elevation of the MRI apparatus 100, taken as indicated by section lines 7-7 FIG. 5 to show an arrangement 170 connecting the movable webs 160, 162 of the treadmill 130 to move together, and additionally showing the mounting of the elongated magnetic structures 120. Within the treadmill 130, each of the webs 160, 162 is held in contact with a roller 172, attached to a shaft 174 turning in bearings 176. Each of the rollers 172 is connected, by means of a belt 178, to a drive shaft 180, which is in turn connected to a motor 182, so that the two movable webs 160, 162 move at the same speed, whether driven by the motor 182 and/or by the moving feet of the patient 108. The movable webs 160, 162 are each further supported by a stationary underlying support structure 184.

At a first end 194 of the MRI apparatus 100, and at a second end 196 thereof, each of the elongated magnetic structures 120 is pivotally mounted in a bushing 198 within an end plate 200, which is moved upward, in the direction of arrow 202, and downward, opposite the direction of arrow 202, by the rotation of a leadscrew 204 engaging an internally threaded structure 205 forming a part of the end plate 200, with the leadscrew 204 being driven by a leadscrew motor 206. Preferably, the leadscrew motors 206 at opposite ends 194, 196 of the MRI apparatus 100 are driven together, with a feedback signal indicating the position of each end plate 200 being developed from a data signal from an encoder 208 reading a scale 210. Each of the end plates slides vertically along a pair of stationary columns 212 by means of bushings 214.

Preferably, each of the elongated magnetic structures 120 extending along an outer edge 220 of the imaging slot 104 is covered by a stationary cover 222, while each of the elongated magnetic structures 120 extending between the imaging slot 104 and the passive space 126 is covered by a stationary lower cover 224 and a movable upper cover 226. These covers 222, 224, 226, which prevent contact between the patient 108 and the elongated magnetic structures 120, may be at least partly composed of thermally insulating materials to restrict outward heat transfer from electrically conducting coils within elongated magnetic structures 120 and/or to restrict an inward flow of heat if coils within the elongated magnetic structures 120 are cryogenically cooled. Preferably, the movable upper cover 226 is attached at each end to one of the end plates 200 to move upward and downward with the elongated magnetic structures 120. In this way, when the elongated magnetic structures 120 are lowered to be aligned with the knee of a shorter patient (not shown) the movable upper cover 226 is also lowered to interfere less with the placement and movement of the legs of the shorter patient. Additionally, the elongated magnetic structures 120 and the upper cover 226 may be lowered to make it easier for the patient 108 to move the leg 124 to be scanned into the imaging slot 104 and to remove the leg 124 therefrom.

It is known that the elongated magnetic structures 120 can be rotated about their axes 230 into various orientations to provide concentrations of flux in various directions within the central region 123, as as described above in reference to FIGS. 2 and 3. Since this effect can be used to optimize the conditions in which a particular joint is scanned to determine the presence of a particular defect, each of the elongated magnetic structures 120 is preferably arranged to be rotationally adjusted. For example, such an adjustment is made by the operation of a motor 228 driving a worm 230 engaging a worm wheel 232 attached to the elongated magnetic structure 120, with an encoder 234 reading a scale (not shown) attached to the worm wheel 232 providing a feedback signal indicating the angular position of the elongated magnetic structure 120.

If the patient 108 faces the first end 194 of the MRI apparatus 100, as shown in FIGS. 5 and 6, the left leg 124 is disposed within the imaging slot 104 for imaging. If the patient 108 faces the second end 196 of the MRI apparatus 100, the right leg 128 is disposed within the imaging slot 104 for imaging. As shown in FIGS. 5 and 6, the MRI apparatus 100 additionally includes a pair of support bars 242 providing handles for use with the treadmill 130, which provide support for the patient 108 when using the treadmill, and which define the area in which the patient 108 runs on the treadmill 130.

Figure 8:
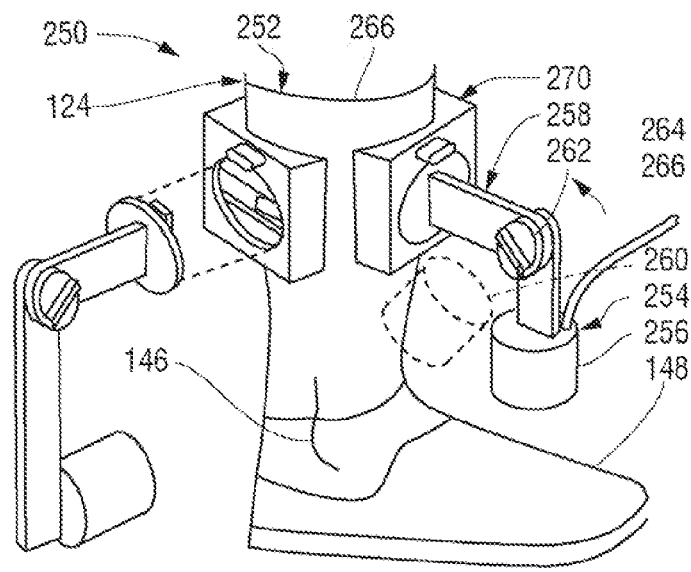
FIG. 8 is a perspective view of probe apparatus for scanning the ankle and foot within the MRI apparatus of FIG. 5.

FIG. 8 is a perspective view of probe apparatus 250 attached to the leg 124 for scanning the ankle 146 and foot 148 within the MRI apparatus 100. The probe apparatus 250 includes a support structure 252 configured for attachment to the leg 124 and, for holding, a first portable probe 254 having a signal receiving portion 256 and an attachment portion 258, which are pivotally attached to one another so that the signal receiving portion 256 can be rotated, for example, between a position in which it is shown, for imaging the foot 148 from above, and a position in which it is indicated by dashed lines 260, for imaging the ankle 146 from an anterior position. A clamping knob 262 is rotated in the releasing direction of arrow 264 to allow pivoting movement of the signal receiving probe 256 relative to the attachment portion 258. Rotation of the clamping knob 262 opposite the releasing direction of arrow 264 locks the signal receiving probe 256 in place on the attachment portion 258. The support structure 252 includes an elastic member 266 and a number of connection members 270, each configured for releasably receiving the attachment portion 258. The elastic member 260 may include may include an elasticized textile material, a solid elastomeric material, and/or a number of belts adjusted to hold the support structure 252 in place on the leg 124. Electrical signals transmitted through wires and/or light signals transmitted through fiber optics and transmitted to remote processing circuits through a cable 268 connected to the signal receiving portion 256.

In FIG. 8, the probe apparatus 250 is shown in an exploded relationship with a second portable probe 272, which is configured for imaging the ankle 146 from a laterally displaced position. For example, the probe position to be used to optimize the scanning process may be determined from the description of symptoms given by the patient and by a physical examination. Preferably, the probe apparatus 250 includes a plurality of connection members 270, each of which is removably connectable with an attachment portion 258 of a plurality of different portable probes, represented herein by the portable probes 254, 272.

FIGS. 9 and 10 show an attachment portion 258 connected to a connection member 270, with FIG. 9 being an elevation of the connection member 270, and with FIG. 10 being a cross-sectional view thereof, taken as indicated by section lines 10-10 in FIG. 9. The attachment portion 258 includes a disk-shaped plug 274, held within a cavity 276 in the connection member 270, and a locking tab 278, that extends beyond edges of a slot 280 within the connection member 270 to prevent removal of the attachment portion 258 from the connection member 270 in the outward direction of arrow 281. The connection member 270 additionally includes a latch 282, movable in and opposite the direction of arrow 281 and held outward, in the engaged position, in which it is shown in FIG. 9, by a spring 284, so that latching surfaces 286 of the latch 282 prevent rotation of the attachment portion 258 in or opposite the direction of arrow 288. For example, the connection member 270 is clamped in place on the elastic member 260 with a clamping plate 290 that is attached to the connection member 270 with a number of screws 292. Preferably, the clamping plate 290 has an inner surface 294 that is concavely curved to fit over the leg 124.

To remove the attachment portion 258 from the connection member 270, first the latch 282 is depressed inward, opposite the direction of arrow 281 by depressing an outward-extending button portion 296 of the latch 282. In this way, the latch 282 is moved into the released position indicated by dashed lines 297, with latching surfaces 286 held away from the locking tab 278 to permit the rotation of the attachment portion 258 in or opposite the direction of arrow 288. Next, the attachment portion 258 is rotated through a ninety-degree angle with the disk-shaped plug 274 rotating within the cavity 278 of the connection member 270, bringing the locking tab 278 into alignment with the slot 280, allowing removal of the attachment portion 258 from the connection member 270 in the outward direction of arrow 281.

Subsequently, the attachment portion 258 can be installed within the connection member 270 by moving the locking tab 278 inward, opposite the direction of arrow 281, through the slot 280 in alignment with the slot 280, and by then turning the attachment portion 258 through a ninety-degree angle in or opposite the direction of arrow 288. As a corner 297 of the locking tab 278 is thus rotated past a ramp 298 within the latch 282, the latch 282 is moved into the released position indicated by dashed lines 292. When the locking tab 258 is moved into the vertical position in which it is shown, the spring 284 restores the latch 282 outward, so that the attachment portion 258 is held in place within the connection member 270.

Thus, it is seen that, in accordance with the first embodiment of the invention, the MRI apparatus 100 is particularly configured for imaging the knee 132, ankle 146, and foot 148 during normal use in walking and running, with a treadmill 130 being provided to limit overall movement of the patient 108 to occur within an imaging slot 104 having sufficient length and height to provide scan these joints whenever the foot 148 is in contact with the treadmill. 130. The elongated magnetic structures 120 extend horizontally, parallel to the treadmill 130, so that the imaging slot 104 is elongated in the direction of movement of the knee 132, ankle 146, and foot 148 with the foot 148 in contact with the treadmill 130. A portable probe for receiving NNR signals keeps the probe close to the knee 132, ankle 146, and foot 148 despite the movement of these joints during the movement of the patient on the treadmill 130. Since the patient 108 straddles two of the elongated magnetic structures 120 while using the treadmill 130, the elongated magnetic structures 120 are also close to both sides of the knee 132, ankle 146, and foot 148. However, the magnetic cannot be moved high enough to provide a magnetic field for imaging the hip 322.

Figure 12:
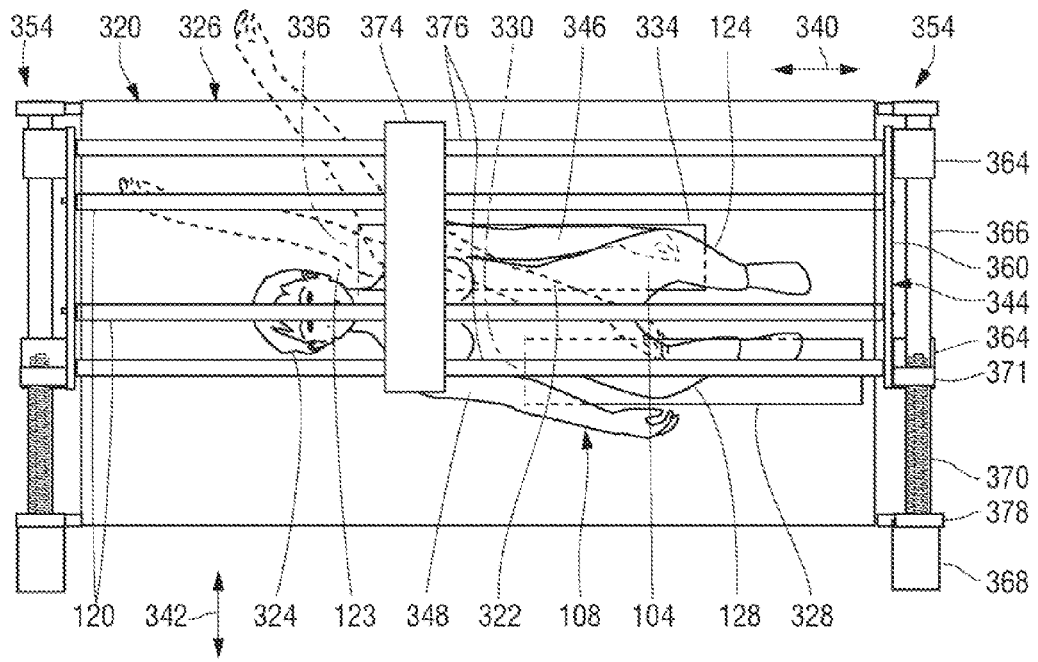
FIG. 12 is a plan view of the MRI apparatus of FIG. 11, used for scanning a shoulder in accordance with the second embodiment of the invention.
Figure 13:
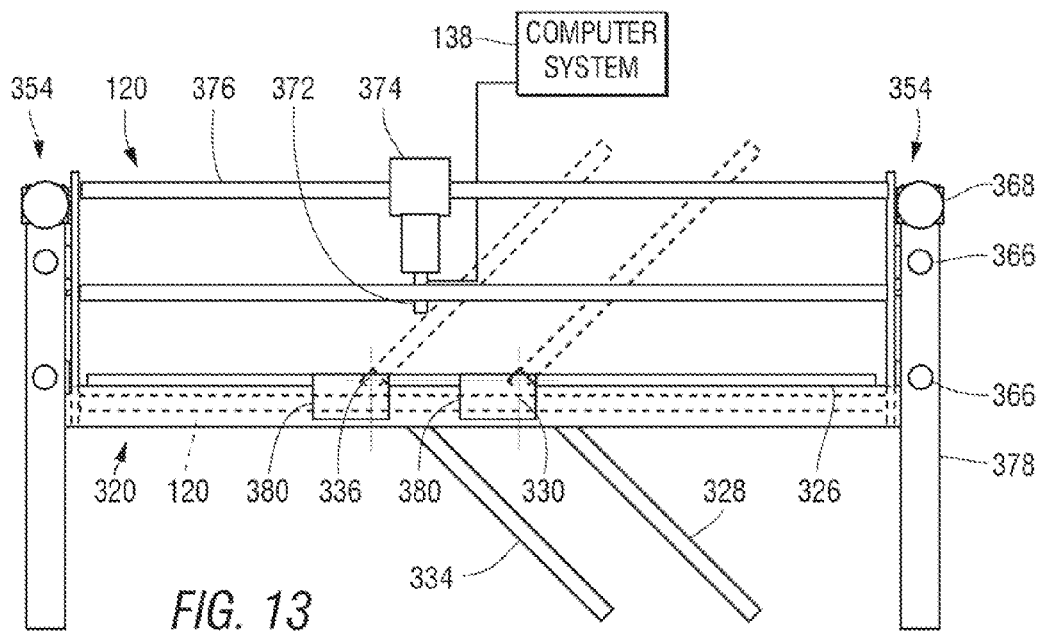
FIG. 13 is a side elevation of the MRI apparatus of FIG. 11.

MRI apparatus 320 built for imaging the hip 322 and shoulder 324 in accordance with a second embodiment of the invention will now be discussed, with particular reference being made to FIGS. 11-13. FIGS. 11 and 12 are plan views of the MRI apparatus 320, with FIG. 11 showing the apparatus 230 being used for imaging a hip 322, and with FIG. 12 showing the apparatus 320 being used for imaging a shoulder 324. FIG. 13 is a side elevation of the MRI apparatus 320. Like the MRI apparatus 100, the MRI apparatus 320 includes four elongated magnetic structures 120 that together form a Halbach array, with centers of the elongated magnetic structures 120 being transversely disposed at corners of a square, with magnetic flux lines extending outward from each of the elongated magnetic structures 120 in the transverse directions of arrows 122, shown in FIG. 6, to be concentrated within a central region 123 as generally described above in reference to FIGS. 1-3, with similar elements being accorded like reference numbers. However, as shown in FIG. 11, the elongated magnetic structures 120 in the MRI apparatus 320 are long enough to allow the patient 108 to lie with his/her leg 124 entirely within an imaging slot 104 formed between the four elongated magnetic structures 120 to include the central region 123.

Furthermore, the MRI apparatus 320 is provided with a table 326 that is used to hold the hip 322 or the shoulder 324 within the central region 123. Preferably, the table 326 includes a leg dropping door 328, pivoted about an axis 330, allowing the leg 124 to be moved downward, into the position indicated by dashed lines 332, and an arm dropping door 334, pivoted about an axis 336, allowing the arm 336 to be lowered as shown by dashed lines 338. Since the leg dropping door 328 and the arm dropping door 334 overlap one another in the longitudinal direction of arrow 340, and are therefore spaced apart in the transverse directions of arrow 342, it is necessary to provide for relative movement between the elongated magnetic structures 120 and the table 326. In the example of the figures, the magnetic strictures 120 are moved between a first position 342, in which they are shown in FIG. 11, with the leg dropping door 328 aligned with the imaging slot 104 for imaging the hip 322, and a second position 344, in which they are shown in FIG. 12, with the arm dropping door 334 aligned with the imaging slot 104 for imaging the shoulder 324. The patient 108 can also be positioned so that either the left arm 346 or the right arm 348 is over the arm dropping door 334 or so that either the left leg 124 or the right leg 128 is over the leg dropping door 328.

In the example of the figures, the elongated magnetic structures 120 are attached at each end 354 to an end plate 360. Each of the end plates 360 is moved in the transverse directions of arrow 342, with bushings 364 attached to the end plates 360 sliding on shafts 366, between the first position 342 and the second position 344, moving through operation of a motor 368 turning a leadscrew 370 engaging a threaded block 371 also attached to the endplate 360. Since the hip 322 and shoulder 324 do not move substantially during the scanning process, it is not necessary to mount a portable probe, such as the portable probe 134 described above in reference to FIGS. 5 and 6, on the body of the patient near the joint being scanned. Therefore, to receive the NMR signals during scanning in the MRI apparatus 320, a movable probe 372 is attached to a carriage 374 that is slid in the longitudinal directions of arrow 340 on a pair of equipment rails 376, which are attached to extend between the end plates 370 so the movable probe 372 will move with the elongated magnetic structures 120. The table 326 and the rails 366 are supported by an underlying frame 378. The portable probe 372 is electrically connected to circuits within the MRI apparatus 370, including a computer system 138 operating as described above in reference to FIG. 5.

Figure 14:
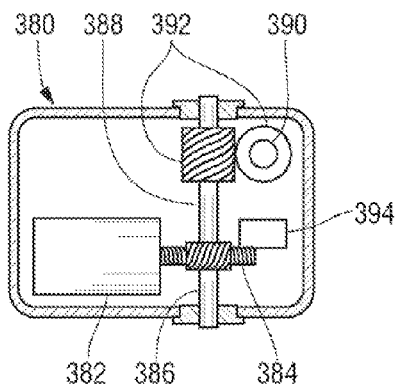
FIG. 14 is a cross-sectional elevation of a mechanism for moving a door within the MRI apparatus of FIG. 11.

FIG. 14 is a cross-sectional elevation of a drive mechanism 380 moving either the leg dropping door 328 or the arm dropping door 334 as a motor 382 turns a worm 384 in response to an operator selection. The worm 384 engages a worm wheel 386 on an intermediate shaft 388 which turns a pivot shaft 390 through a pair of helical gears 392. An encoder 394, sensing markings on the worm wheel 344, provides a feedback signal indicating the position of the door 328, 332 being moved. The pivot shaft 390 is directly connected to the door 328, 334, forming a pivot axis as well as a source of angular movement. With the drive mechanism 380, the door 328, 334 can be used to raise and lower the arm 346 or the leg 350 at various speeds or through selected incremental movements. Alternately, the door 328, 334 may simply be moved out of the way so that the patient 108 or an assistant (not shown) can apply movements to the arm 346 or to the leg 350.

Figure 15:
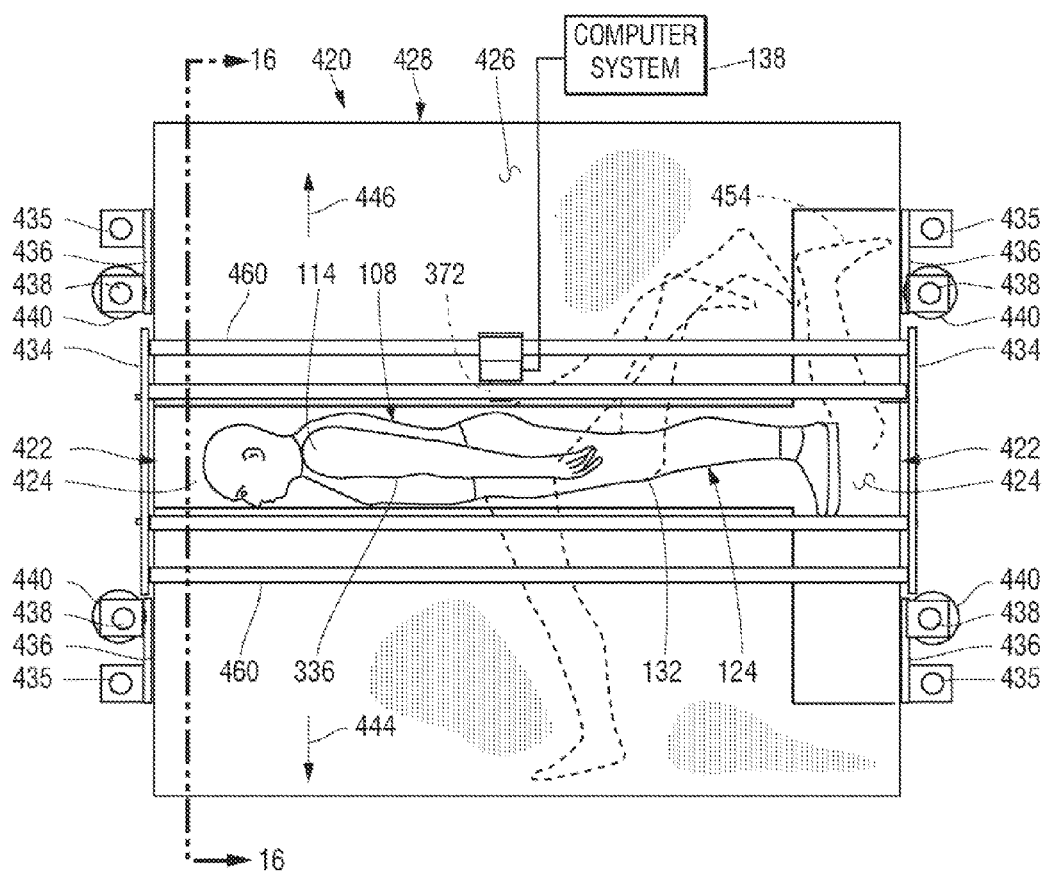
FIG. 15 is a plan view of MRI apparatus built and used in accordance with a third embodiment of the invention.
Figure 16:
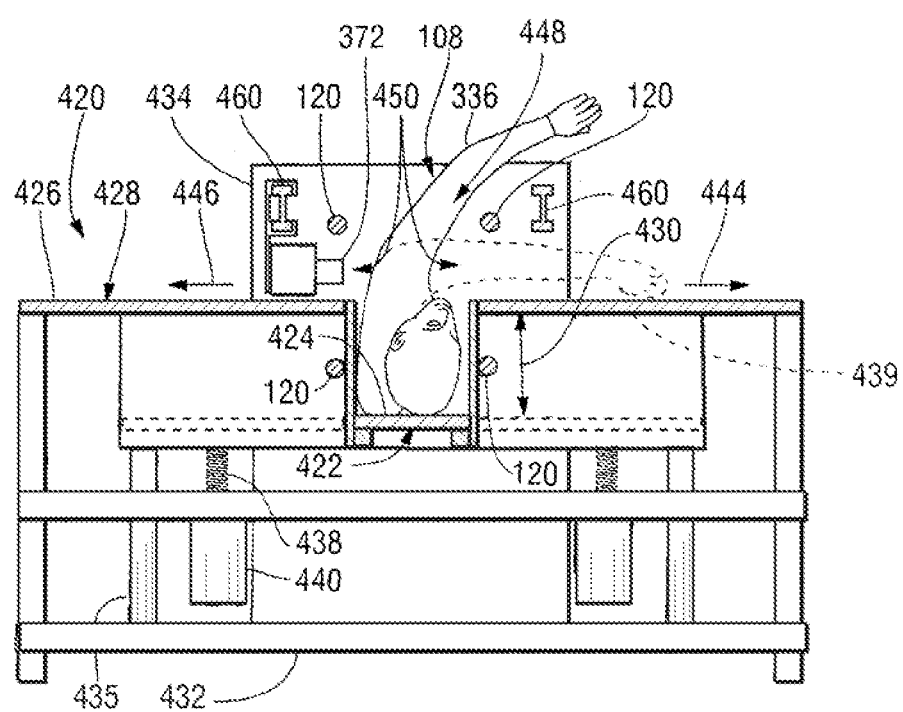
FIG. 16 is a transverse cross sectional elevation of the MRI apparatus of FIG. 15, taken as indicated by section lines 16-16 therein.

A third embodiment of the invention will now be discussed, with reference being made to FIGS. 15 and 16. FIG. 15 is a plan view of MRI apparatus 420 made and used in accordance with the third embodiment of the invention, while FIG. 16 is a cross-sectional elevation thereof, taken as indicated by section lines 16-16 in FIG. 15. In accordance with the third embodiment of the invention, the patient 108 is placed on his or her side on a platform 422 having an upper surface 424 that is disposed below the upper surface 426 of an adjacent bifurcated table 428 through a distance 430 that provides for movement of an inner surface 439 if an arm 336 or a leg 124 along the table 428. Since this distance 430 varies from one patient 108 to another, the MRI apparatus 420 is preferably provided with a means for adjusting this distance 430. In the example of the figures, the table 428 and the elongated magnetic structures 120 are supported by an underlying stationary framework 432 and stationary end plates 434, while the platform 422 is mounted to move vertically along a number of columns 435, extending between movable end plates 436 and being driven by leadscrews 438 rotated by motors 440

When the patient 108 lies on his or her right side 442, as shown in the FIGS. 15 and 16, his or her left shoulder 114 can be scanned while his or her left arm 336 is moved outward, between the uppermost elongated magnetic structures 120, as shown in in FIG. 16, forward along the table 428 in the in the direction of arrow 444, or rearward, along the table 428 in the direction of arrow 446. Additionally, his or her left elbow 324 can be imaged as it is bent or straightened with the lower arm 448 is moved upward, forward, or rearward. Furthermore, as the patient 109 lies on his or her right side 442, the left hip 322 and left knee 132 can be scanned as the patient moves his left leg 124, or a lower portion 446 thereof outward, forward, or rearward. Joints in the right arm 348 and the right leg 128 (shown in FIG. 12) are similarly scanned with the patient 108 lying on his or her left side 446.

Thus, in both the MRI apparatus 320 built inn accordance with the second embodiment of the invention and the MRI apparatus 420 built in accordance with the third embodiment of the invention, advantage is taken of an upwardly-directed slot 448 extending between the uppermost elongated magnetic structures 120, and of a laterally-directed slot 450 extending between the magnetic structures 120 at each side of the central region 123, with the patient being able to move all or part of an arm 336, 348 or leg 126, 128 away from the central region 123 a joint associated therewith remains in the central region 123 for scanning.

Preferably, the MRI apparatus 420 is long enough in the longitudinal directions of arrow 340 to the leg 124 to be fully extended and swung along the table 428 into positions indicated by dashed lines 452, with the head 454 held on the platform 211. As shown in the figures, the platform may be T-shaped, allowing a lower portion 454 of a leg to be held therein with the body of the patient 108 moved in the direction of arrow 446 to provide room to move the arm 326 above the head 458. The MRI apparatus 420 additionally includes an equipment rail 460, extending between the stationary end plates 434, outwardly disposed from each side of the central region 123 for movably mounting a probe 372 used to receive NMR signals used within the scanning process. The portable probe 372 is electrically connected to circuits within the MRI apparatus 420, including a computer system 138 operating as described above in reference to FIG. 5.

Figure 17:
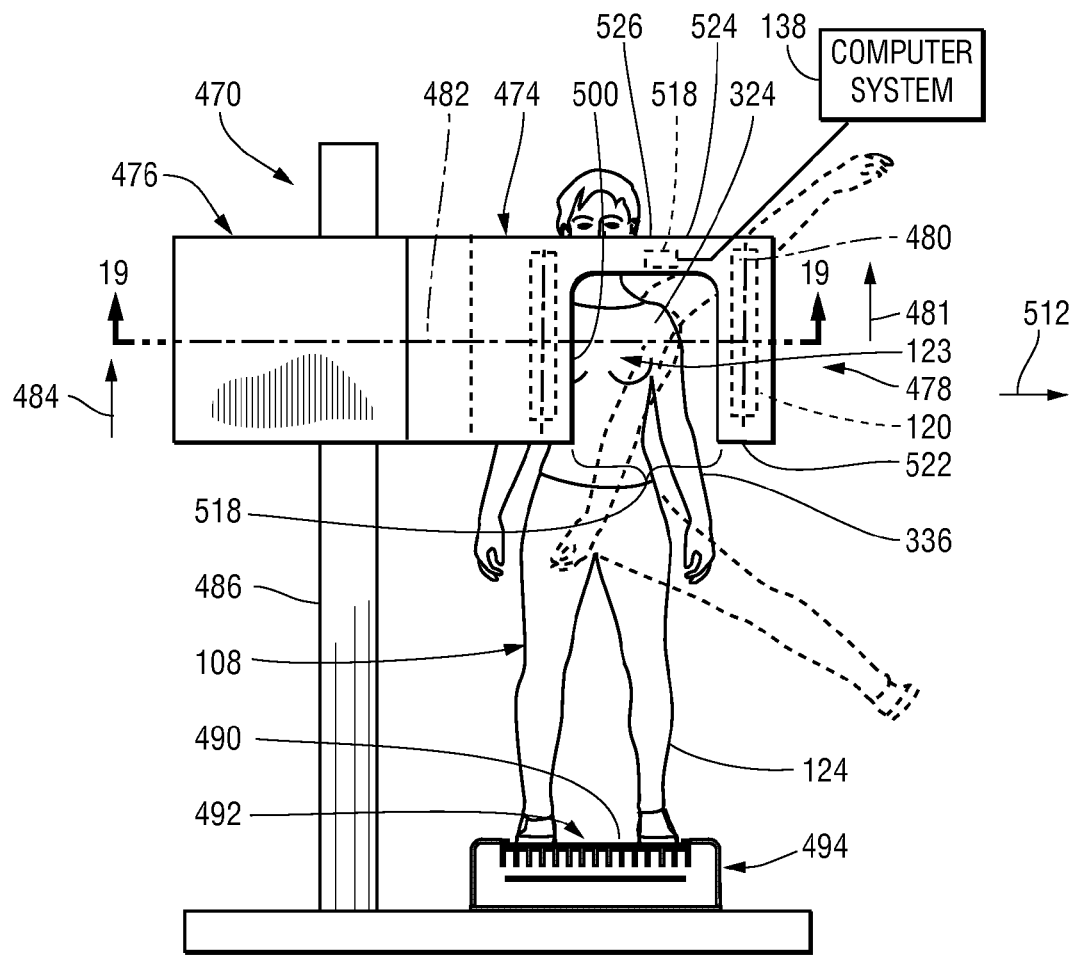
FIG. 17 is a partly sectional end elevation of MRI apparatus built and used in accordance with a fourth embodiment of the invention, shown as arranged for scanning a shoulder.
Figure 18:
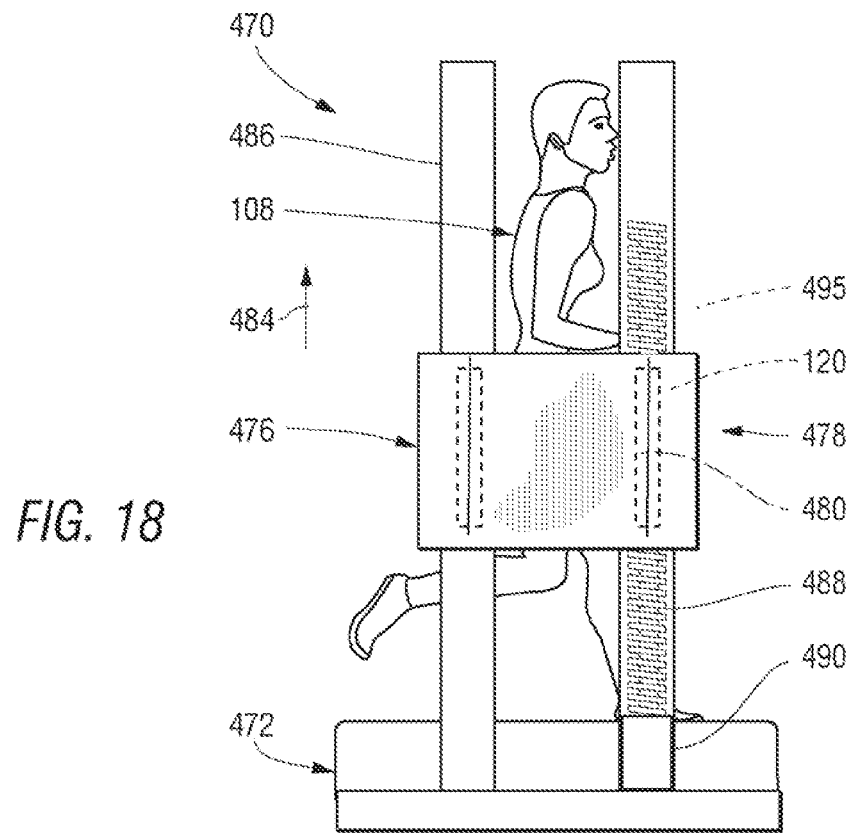
FIG. 18 is a rear elevation of the MRI apparatus of FIG. 17, shown as used for scanning a hip.
Figure 19:
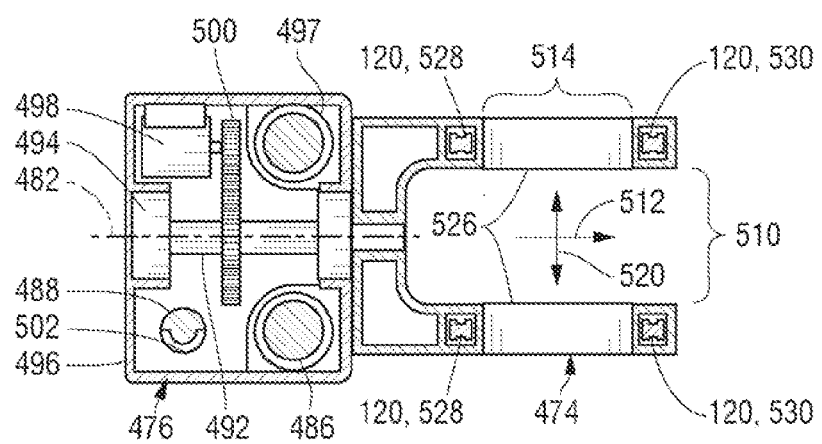
FIG. 19 is a cross-sectional bottom plan view of a carriage within the MRI apparatus of FIG. 17.

A fourth embodiment of the invention will now be discussed, with reference being made to FIGS. 17-19. FIGS. 17 and 18 show the MRI apparatus 470 as used with a treadmill 472 in a first orientation. FIG. 17 has an end elevation thereof, while FIG. 18 is a rear elevation thereof. FIG. 19 is a cross-sectional bottom plan view of a carriage 474 and a rotational drive unit 476 within the MRI apparatus 470, taken as indicated by section lines 19-19 in FIG. 17. In accordance with the fourth embodiment of the invention, a Halbach magnet array 478 is mounted within the carriage 474, with the magnetic structure axes 480 of the elongated magnetic structures 120 within the Halbach magnet array 478 being parallel to one another, extending in the common direction indicated by arrow 481, and being separated from one another in the form of a square. The carriage 474 is pivotally attached to the rotational drive unit 476 to rotate about a pivot axis 482 that is, for example, perpendicular to the common directions of arrow 481, so that rotation of the carriage 474 causes the rotation of each of the elongated magnetic structures 120. The rotational drive unit 476 is in turn mounted to slide upward, in the direction of arrow 484, and downward, opposite the direction of arrow 484, along a pair of columns 486, being driven upward and downward by a leadscrew 488, turned by a motor 490.

As shown particularly in FIG. 19, the carriage 474 is pivotally attached to the rotational drive unit 476 by a pivot shaft 492 extending along the pivot axis 482 through bearings 494 held within a housing 496 of the rotational drive unit 476, with a motor 498 within the housing 496 turning the pivot shaft 492 through a gear train 500. Movement of the rotational drive unit 476 along the columns 486, along which bushings 497 within the housing 496 slide, is provided by engagement between the leadscrew 488 and a threaded surface 502 within the housing 496.

Referring to FIGS. 17 and 19, the carriage 474 includes a first slot 510, extending outward within the carriage 474, parallel the pivot axis 482, in the outward direction of arrow 512, a second slot 514, extending through the carriage 474 perpendicular to the pivot axis 582 and perpendicular to the common direction of the magnetic structure axes 480, and a third slot 518, extending through the carriage 474, perpendicular to the pivot axis 480 and parallel to the common direction of the magnetic structure axes 480. The carriage 474 is also characterized as having an open end 522 and an obstructed end 524, which is partially obstructed by structural members 526, extending between the innermost magnetic structures 528 and the outermost magnetic structures 530.

FIGS. 17 and 18 show the MRI apparatus 470 with the patient's body 108 facing in a direction of arrow 532, perpendicular to the pivot axis 482, and with the open end 522 of the carriage 474 facing downward to minimize obstructions to movement of an arm 336 or a leg 124 extending downward from the carriage 474. The treadmill 494 is additionally arranged for use by a person facing in the direction of arrow 532. FIG. 17 additionally shows the carriage 474 held in position to scan the shoulder 324, with the arm 336 being moved outward, in the direction of arrow 512 and upward through the slot 510, or forward and rearward, in the directions of arrow 520 (shown in FIG. 19) through the slot 514. FIG. 18 additionally shows the carriage 474 held in position to scan the hip 322, with the leg 124 being moved outward through the slot 510 or forward and rearward through the slot 514.

FIG. 20 is a partly sectional front elevation showing the MRI apparatus 470 as used for scanning a knee, with the patient's body 108 facing outward, in the direction of arrow 512, away from the columns 486 and parallel to the pivot axis 482. The treadmill 494 is arranged to be used by a person facing in the outward direction of arrow 510. The carriage 474, which is shown in a cross-sectional view, is rotated so that the open end 522 is facing upward, with the structural members 526 being held at the bottom of the carriage 474, allowing one of the structural members 536 to be straddled for imaging the knee 132 within an imaging slot 104 within the magnetic structures 120 while the patient walks or runs on the treadmill 494. Because the knee 132 moves through significant distances with walking or running on the treadmill 494, a portable probe 134 connected to circuits including a computer system 138, is fastened to the leg 124 to detect NMR signals, as described above in reference to FIGS. 5 and 6. The treadmill 494 may include a handle 548 as shown, or a handle may be placed on the carriage 474.

Figure 22:
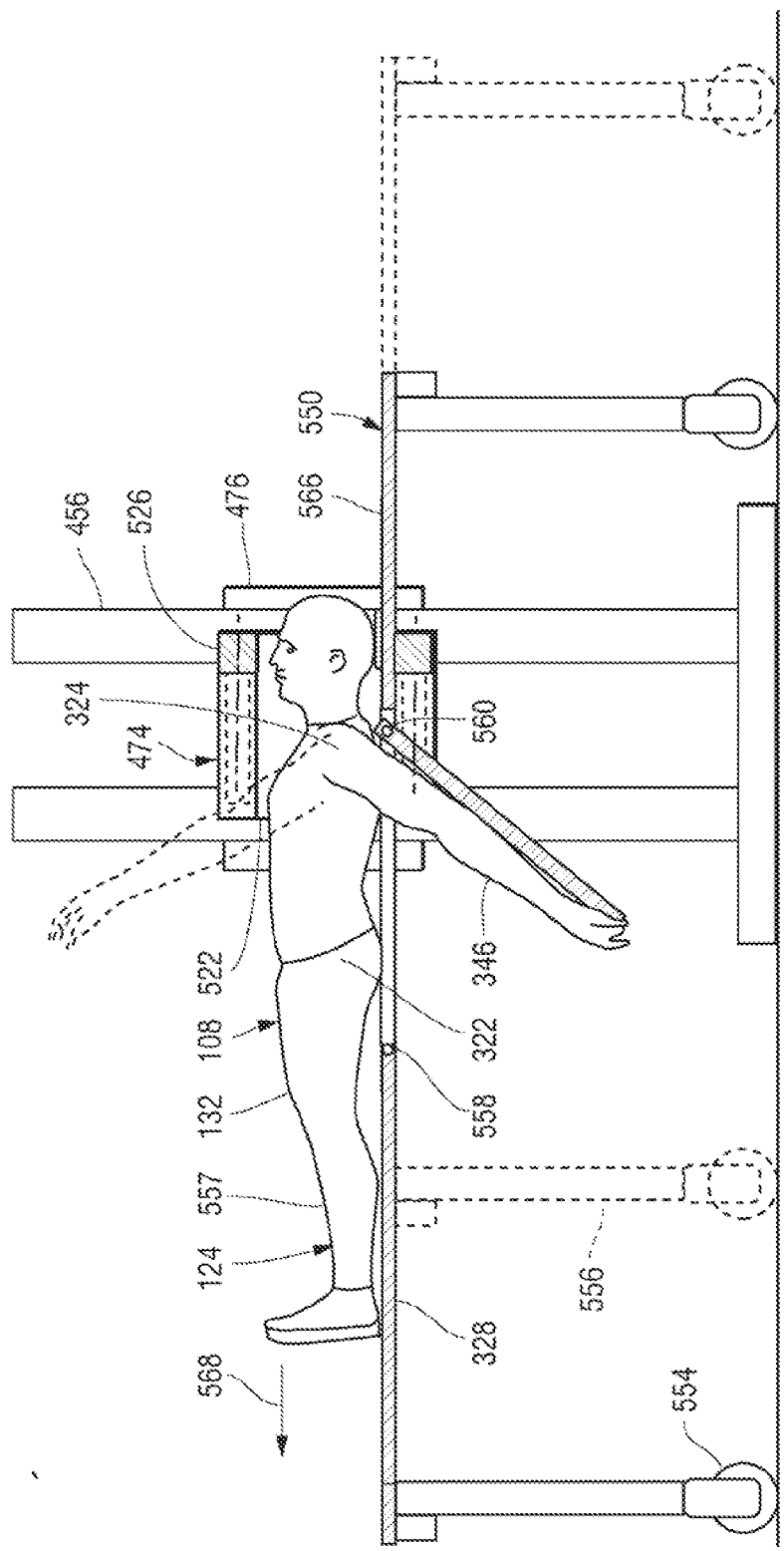
FIG. 22 is a front elevation of the arrangement of FIG. 21, shown as used for scanning a shoulder.

FIGS. 21 and 22 show the MRI apparatus 470 in use with a table 550, upon which the patient's body 108 is placed for certain scanning procedures. FIG. 21 is an end elevation of the MRI apparatus 470 with the table 550 in place, while FIG. 22 is a front elevation thereof. The table 450 includes an arm dropping door 334 and a leg dropping door 328, functioning as similar elements having similar reference numbers described above in reference to FIGS. 11 and 12 allowing the shoulder 324 to be scanned as the arm 346 is moved, and allowing the hip 322 to be scanned as the leg 124 is moved. In the example of the figures, the arm dropping door 334 is shown as lowered, while the leg dropping door 328 is shown as held flush with the table surface 552. A probe 553, fastened to the carriage 474, directs an output signal to a computer system 138.

Preferably, the MRI apparatus 470 and the table 550 are configured to allow relative motion between them. For example, the table 550 may be provided with wheels 554, allowing the table 550 to be moved between a first position, in which it is shown, with the arm dropping door 334 in position for scanning the shoulder 324 as the arm 346 is moved, and a second position, in which it is indicated by dashed lines 556, with the pivot 558 of the leg dropping door 328 in the position of the pivot 560 of the arm dropping door 334 as shown in FIG. 22, so that the leg dropping door 378 in position for scanning the hip 322 as the leg 124 is moved. Furthermore, with the table 550 in the position indicated by dashed lines 556, the patient's body can be moved into position for scanning the knee 132 as the lower leg 557 is moved.

The carriage 474 is rotated into a position with the open end 522 facing a longitudinal direction 562 along the length of the table 550, so that the arm 346 and the arm dropping door 334, or, alternately, the leg dropping door 378 and the leg 124, can move upward and downward through open space, with minimal interference from the structural members 526 or from other parts of the carriage 474.

The table 550 includes an inner portion 564 and an outer portion 566, disposed at opposite sides of the arm dropping door 334 and the leg dropping door 378, with the inner portion 564 being disposed closer to the columns 496. The patient's body 108 may be placed on the inner portion 564, with the left arm 346 extending along the arm dropping door 334, or with the left leg 124 extending along the leg dropping door 378. Alternately, joints on the right side of the patient's body 108 may be scanned by placing the patient's body 108 on the outer portion 566, with the right arm 348 extending along the arm dropping door 334, or with the right leg 128 (both shown in FIG. 20) extending along the leg dropping door 378.

Figure 23:
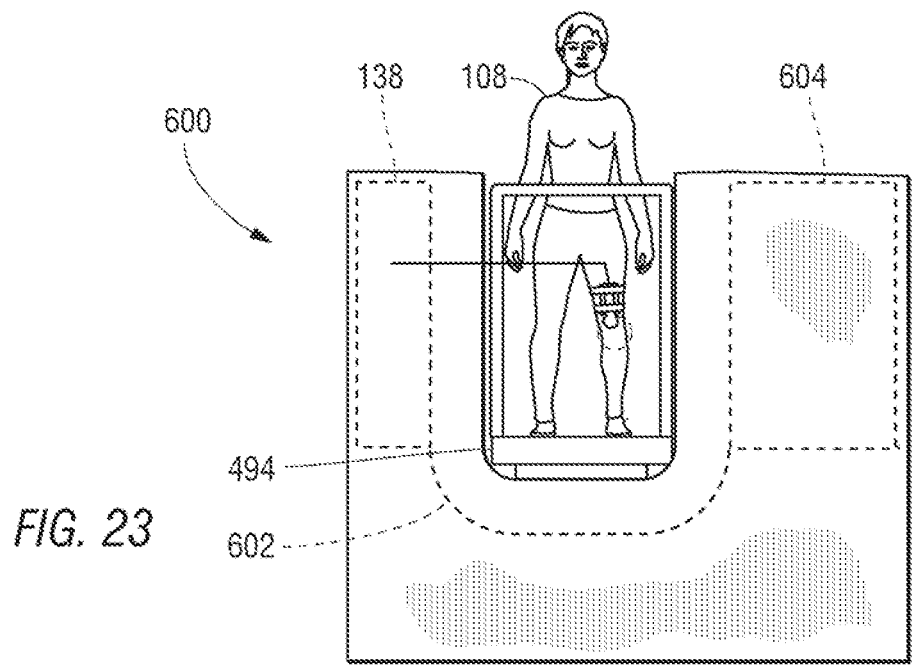
FIG. 23 is a front elevation of MRI apparatus including a U-shaped magnetic structure, shown as used with a treadmill for scanning a knee.
Figure 24:
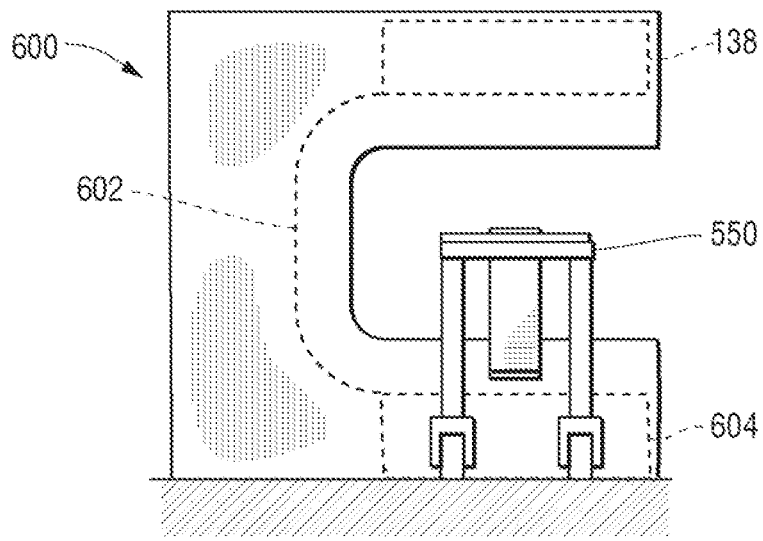
FIG. 24 is an end elevation of the MRI apparatus of FIG. 23, shown as used with a table in accordance with the invention.
Figure 25:
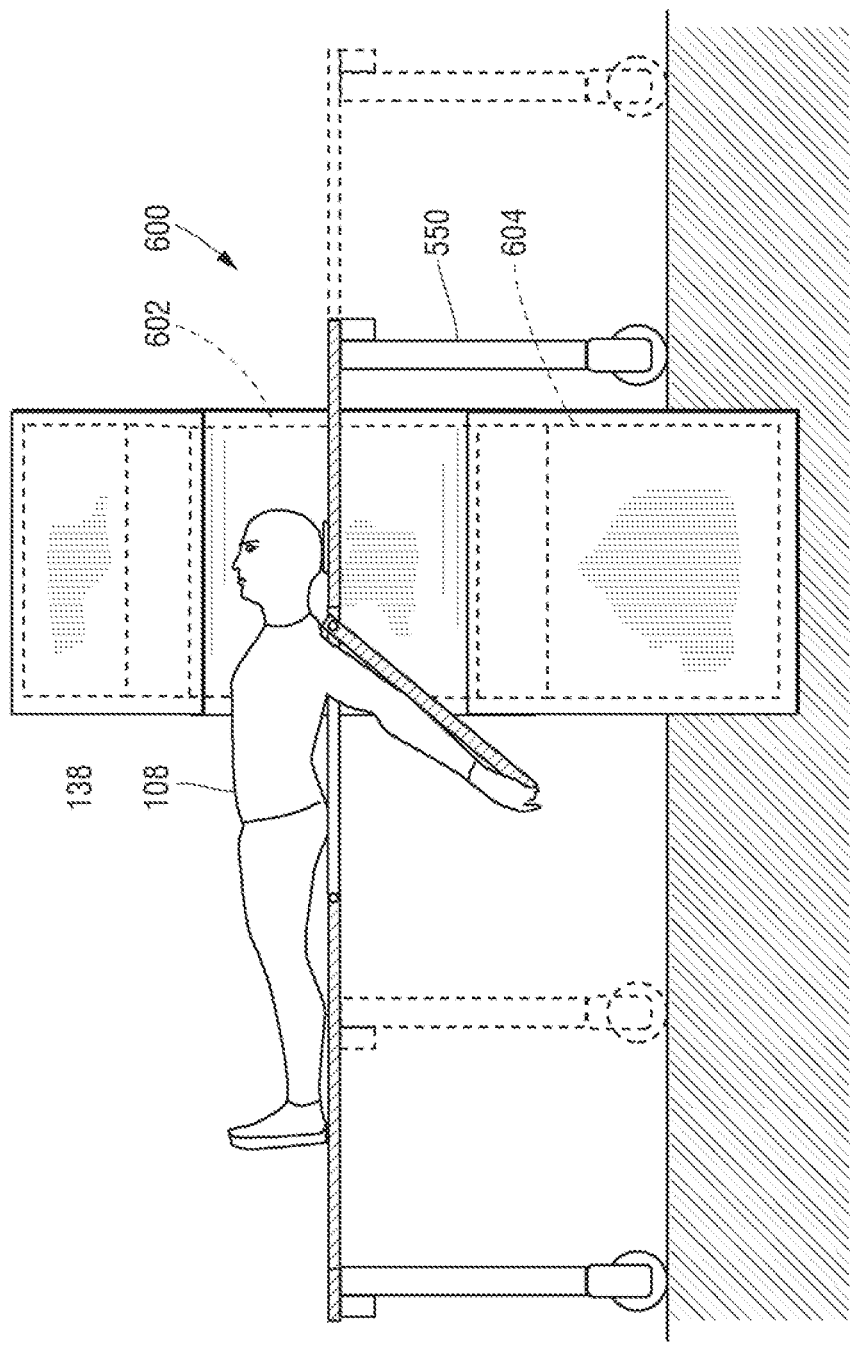
FIG. 25 is a front elevation of the arrangement of FIG. 24, shown as used for scanning a shoulder.

As shown in FIGS. 23-25, various versions of the apparatus and methods of the invention can be used with MRI apparatus 600 including a U-shaped overall magnetic structure 602, with all or part of the patient's body being placed within a central region 123 therein. The MRI apparatus 600 additionally includes circuits 604 causing the magnetic structure 602 to generate magnetic fields within the central region 123 and a computer system 138 generating images from signals transmitted from a portable probe 134 fastened to the patient's body 108, as described above in reference to FIG. 5, or from a probe (not shown) otherwise held within the apparatus 600. FIG. 23 is an end elevation of the MRI apparatus 600 in use with a treadmill 494, as described above in reference to FIG. 17. FIGS. 24 and 25 show the MRI apparatus 600 in use with a table 550, as described above in reference to FIGS. 21 and 22, with FIG. 24 being an end elevation thereof, and with FIG. 25 being a front elevation thereof.

For example, the use of one of the embodiments described above begins with the patient describing a problem as occurring in a joint area when a body part connected to the joint is moved into a particular position. For example, the problem may be pain or stiffness. All or part of the body 108 of the patient is then placed in one of the versions of MRI apparatus described above, with the joint area within the central region 123, of the apparatus and with provision being made for movement of the body part connected to the joint into the particular position described. Such provision may be a treadmill 130, 472, 494, allowing the leg 124 to be moved, or a surface supporting the body part as it is moved. As the body part is moved into the particular position, a probe 134, 518 detects nuclear magnetic resonance (NMR) signals and transmits an output signal to a computer system 138 that generates a series of images describing the joint. Preferably, these images are generated in real time, or at least fast enough that they provide feedback to the method being used.

It is understood that, while various elements and features have been described with some degree of particularity, such descriptions have been given only by way of example, and that many variations are possible within the spirit and scope of the inventions, which is understood to be limited only by the appended claims.

What is claimed is:

1. A method for examining a joint region within a patient, wherein the method comprises;
    a) determining that a problem develops within the joint region when a first body part adjacent the joint region is moved into a particular position;
    b) placing the joint rejoin in a central region within magnetic resonance imaging (MRI) apparatus including a magnetic structure disposed at each side of the central region, and an additional place adjacent the central region, with the body part disposed within the additional space, wherein the joint region moves substantially within the central region as the body part is moved into the particular position;
    c) attaching a probe assembly to the patient's body adjacent the joint region to move with the joint region;
    d) moving the body part adjacent the joint region into the particular position while causing a nuclear magnetic resonance (NMR) signal to be formed within the central region;
    e) receiving the NMR signal within a probe assembly within the central region and transmitting a signal including data describing structures within the joint region from the probe assembly; and
    f) generating and displaying a viewable image of the joint region from the signal transmitted from the probe assembly.

2. The method of claim 1, wherein the body part is moved into the particular position as the patient walks or runs on a treadmill disposed within the additional area.

3. The method of claim 2, wherein the patient straddles a central structure including a portion of the magnetic structures while walking or running on the treadmill.

4. The method of claim 1, wherein
    the method additionally comprises, before step d), placing the patient on a table extending within the MRI apparatus adjacent the central region, and
    a door within the table is lowered to allow the body part adjacent the joint region to be moved into the particular position.

* * * * *